US006387528B1

(12) United States Patent
Pomplun et al.

(10) Patent No.: US 6,387,528 B1
(45) Date of Patent: May 14, 2002

(54) COMPOSITIONS OF ION-TRIGGER POLYMER COATINGS ON WATER-SENSITIVE POLYMER FILMS

(75) Inventors: William S. Pomplun, West End, NC (US); John E. Kerins, Neenah, WI (US); Pavneet S. Mumick, Belle Mead, NJ (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/427,791

(22) Filed: Oct. 27, 1999

Related U.S. Application Data

(60) Provisional application No. 60/114,213, filed on Dec. 29, 1998.

(51) Int. Cl.$^7$ .................................... B32B 23/08

(52) U.S. Cl. ..................... 428/508; 428/481; 428/507; 428/510; 428/335; 428/534; 264/510; 427/401

(58) Field of Search .......................... 428/411.1, 480, 428/483, 532, 500, 507, 533, 534, 481, 508, 510, 335

(56) References Cited

U.S. PATENT DOCUMENTS

| | | | | |
|---|---|---|---|---|
| 3,901,838 A | | 8/1975 | Clendinning et al | 523/126 |
| 3,921,333 A | | 11/1975 | Clendinning et al. | 47/74 |
| 3,935,141 A | | 1/1976 | Potts et al. | 524/322 |
| 3,951,893 A | | 4/1976 | Gander | 524/322 |
| 4,372,311 A | | 2/1983 | Potts | 604/364 |
| 4,868,024 A | | 9/1989 | Cross et al. | 428/35.2 |
| 4,910,292 A | | 3/1990 | Blount | 528/272 |
| 4,990,593 A | | 2/1991 | Blount | 528/272 |
| 5,015,245 A | | 5/1991 | Noda | 604/367 |
| 5,300,358 A | | 4/1994 | Evers | 442/396 |
| 5,317,063 A | | 5/1994 | Komatsu et al. | 525/330.2 |
| 5,505,830 A | | 4/1996 | Petcavich | 204/157.63 |
| 5,509,913 A | | 4/1996 | Yeo | 604/364 |
| 5,543,488 A | | 8/1996 | Miller et al. | 528/277 |
| 5,578,344 A | | 11/1996 | Ahr et al. | 427/211 |
| 5,658,977 A | | 8/1997 | Yang et al. | 524/503 |
| 5,770,528 A | * | 6/1998 | Mumick et al. | 442/59 |

FOREIGN PATENT DOCUMENTS

| | | |
|---|---|---|
| EP | 0 142 950 | 5/1985 |
| EP | 0 361 842 | 4/1990 |
| EP | 0 761 795 | 3/1997 |
| EP | 0 781 538 | 7/1997 |
| EP | 0 761 795 A2 | 12/1997 |
| GB | 1 211 095 | 11/1970 |
| JP | 55108357 | 8/1980 |
| JP | 6245954 | 9/1994 |
| JP | 6245956 | 9/1994 |
| WO | WO 91/14413 | 10/1991 |
| WO | WO 93/04653 | 3/1993 |

* cited by examiner

*Primary Examiner*—Blaine Copenheaver
*Assistant Examiner*—Christopher Paulraj
(74) *Attorney, Agent, or Firm*—Kilpatrick Stockton LLP

(57) ABSTRACT

The present invention provides a composition comprising an ion-trigger polymer coating joined to a water-sensitive substrate. When the composition is employed as a diaper outercover or a pantiliner baffle, for example, the ion-trigger coating is oriented toward the body and is exposed to bodily fluids. The coating inhibits the transport of the fluids to the inner, body-side water-sensitive substrate, maintaining the structural integrity of the composition. When the entire article is disposed of in a large volume of water, such as in the hydraulic flow of a toilet, both the water-sensitive substrate layer and the ion-trigger polymer coating layer mechanically weaken and break apart into small pieces.

24 Claims, No Drawings

COMPOSITIONS OF ION-TRIGGER POLYMER COATINGS ON WATER-SENSITIVE POLYMER FILMS

CROSS-REFERENCE TO RELATED APPLICATION

This application claims priority to U.S. Provisional Patent Application Serial No. 60/114,213, filed Dec. 29, 1998.

FIELD OF THE INVENTION

The present invention relates to polymer compositions that are water stable on one surface and water-sensitive on the opposing surface. More particularly, the present invention encompasses flushable, barrier films that retain their integrity in the presence of body waste fluids, but which disintegrate and disperse in the hydraulic flow of a toilet.

BACKGROUND OF THE INVENTION

Disposable products have revolutionized modern lifestyle and are of great convenience to society. Such products generally are relatively inexpensive, sanitary and quick and easy to use. Disposal of such products, however, increasingly is a problem as landfills close and incineration contributes to urban smog and pollution. Consequently there is an urgent need for disposable products that can be disposed of without dumping or incineration. An ideal disposal alternative would be the use of municipal sewage treatment and private residential septic systems. Products suited for disposal in sewage systems that can be flushed down a conventional toilet are termed "flushable." An essential feature of flushable products is that they must have sufficient strength for their intended use, yet lose structural integrity upon contact with water. Meeting these dual criteria is particularly difficult for products that come in contact with body waste fluids, especially urine.

Numerous attempts have been made to produce flushable fibers, fabrics, films and adhesives that retain their integrity and wet strength in the presence of body waste fluids, yet can be disposed of via flushing in conventional toilets. One approach to producing a flushable product is to limit the size of the product so that it will readily pass through plumbing without causing obstructions or blockages. Such products may have high wet strength and would not disintegrate during flushing. Examples of this type of product might include wipes such as baby wipes. This approach to flushability suffers the disadvantage, however, of being restricted to small sized articles. Many of the current flushable products are limited to such small articles.

Another approach to producing a flushable product is to manufacture a product that is normally insoluble in water, but which disintegrates in the presence of alkaline or acidic aqueous solutions. The end user is provided with an alkaline or acidic material to add to the water in which the product is to be disposed. This approach permits disposal via normal plumbing systems of products substantially larger than wipes, but suffers from the disadvantage of requiring the user to perform the step of adding the dissolving chemical to the water. A further disadvantage is that the inadvertent or intentional disposal of such a product in a conventional toilet without the addition of the dissolving chemical can cause serious obstruction or blockage of the plumbing system. The latter disadvantage can, however, be overcome by incorporating the dissolving acid or alkali into the article but separate from the dissolvable material while in use. The dissolving chemical is only released upon contact with water during flushing.

Similarly, another approach to producing a flushable product consists of forming the product from a pH sensitive polymer and storing the product in the presence of a separate acid pH solution. When the product is placed in a large quantity of normal tap water, it disintegrates as a result of the pH shift. A disadvantage of this pH shift approach to flushability is that some acidic polymers lose wet strength at slightly alkaline pH in the range of 7–8. Because the pH of urine may be as high as 8.5, these flushable materials may not be well suited for use in, for example, diapers or incontinence pads.

Yet another approach to producing a flushable product is to form the product from material that is susceptible to attack by specific enzyme catalysis that breaks down the structural integrity of the material. In such a product the enzymes may be introduced into the disposal water separately. These systems suffer many of the same problems as acid or alkaline treatable materials.

Still others have attempted to make flushable products wherein a non-woven web is bound together with salt-sensitive binders. For example, some acrylic copolymers precipitate in the presence of high concentrations of calcium ions. The problem with calcium-dependent water soluble binders, however, is that across the country the concentration of calcium in normal tap water varies tremendously. Consequently, flushable products made with those binders may not, in fact, be flushable in regions with high calcium containing water.

None of the above approaches have proven completely satisfactory. Therefore, there is a need for a flushable barrier product which is stable in ion-containing bodily fluids, and which does not require special conditions of disposal.

SUMMARY OF THE INVENTION

The present invention provides a composition comprising a an ion-trigger polymer coating joined to a water-sensitive substrate. When the composition is employed as a diaper outercover or a pantiliner baffle, for example, the inner, body-side ion-trigger coating is exposed to bodily fluids, and acts as a barrier coating thereby inhibiting their transport to the lower water-sensitive substrate, maintaining the structural integrity of the composition. When the entire article is disposed of in a large volume of water, such as in the hydraulic flow of a toilet, both the water-sensitive substrate layer and the ion-trigger polymer coating layer mechanically weaken and break apart.

The present invention is, therefore, desirably designed to provide disposable compositions that can be flushed in a conventional toilet. It is also desirable to provide disposable compositions that act as fluid barriers, but are also capable of being flushed in a conventional toilet without the addition of a dissolving chemical. Additionally, it is desirable to provide flushable compositions that are insoluble in the presence of body waste fluids, but which are water dispersible in the presence of normal toilet water. Also, it is desirable to provide flushable compositions that disintegrate and disperse in normal toilet water regardless of geographic variations in toilet water salt concentrations. Additionally, it is desirable to provide flushable compositions that have sufficient strength for their intended use. Finally, it is desirable to provide flushable products, including, but not limited to, feminine care products, diapers and training pants, bandages, packaging, release films, and the like.

DETAILED DESCRIPTION OF THE INVENTION

The present invention provides a composition comprising an ion-trigger polymer coating joined to a water-sensitive substrate. When the composition is employed as a diaper outercover or a pantiliner baffle, for example, the inner ion-trigger coating is exposed to bodily fluids, and acts as a barrier coating, thereby inhibiting their transport to the lower water-sensitive substrate, maintaining the structural integrity of the composition. When the composition is disposed of in a large volume of water, such as in the hydraulic flow of a toilet, both the water-sensitive substrate layer and the ion-trigger polymer coating layer mechanically weaken and break apart.

Therefore, one embodiment of the present invention provides a composite two-layer article comprising an ion-trigger coating on a water-sensitive substrate. In normal use, it is understood that the inner, ion-trigger coated side of the article will typically be exposed to bodily fluids, such as blood, menstrual fluid, vaginal exudate, urine and perspiration. The term "inner side", as used herein, means the side of the film closest to the skin of the wearer. Both the inner ion-trigger coating and the outer, water-sensitive substrate will be exposed to toilet water during disposal. The ion-trigger coating on the inner side acts as a barrier coating and inhibits the transport of body fluids from the wearer through the article, effectively providing a barrier between body fluids and the water-sensitive substrate.

In a further embodiment of the present invention, the composition may serve as a primer layer for additional coatings on the water-sensitive substrate, such as latex coatings or a second layer of an ion-trigger material. The primer layer provides enough water protection so that a water-based solution coating may be applied to the coated water-sensitive film, the water being subsequently removed prior to any degradation of the water-sensitive substrate layer. In most cases and applications, the coated water-sensitive film is flushable and dispersible because it will disintegrate rapidly when exposed to the flow of water such as in a conventional toilet.

Flushable articles of the present invention may be made up entirely of flushable components, or composed of a mixture of flushable and non-flushable materials. In the former case, the entire article disintegrates or disperses in the hydraulic flow of normal toilet water, while in the latter case the flushable components disperse in the presence of normal toilet water. The flushable article falls apart into pieces small enough to be flushed without causing obstruction.

The term "flushable" as used herein means capable of being flushed in a conventional toilet, and being introduced into a municipal sewage or residential septic system, without causing an obstruction or blockage in the toilet or sewage system, and does not adversely affect the microbiology of the septic or sewage treatment system. The term "flushable article" as used herein includes, but is not limited to, feminine care products, diapers and training pants, bandages, packaging, release films, and the like.

Several formulations of the ion-trigger polymer coating may be used with the present invention. In order to be effective for use in flushable personal care products, the ion trigger coating must be functional in use, i.e. maintain integrity and act as a barrier in the presence of body fluids, yet dissolve or disperse rapidly in water found in toilets. The main component of the ion-trigger coating of the present invention is an ion-trigger polymer. An ion-trigger polymer is one whose strength and dispersibility in water is changed depending on a very slight difference in the concentrations of a salt. More specifically, an ion-trigger polymer loses strength and disperses in tap water, but maintains strength and is insoluble in an aqueous solution which contains not less than 0.5% by weight of a neutral inorganic salt comprising a monovalent ion such as NaCl, KCl and NaBr.

It is well known that addition of an inorganic salt to an aqueous solution of a water soluble polymer may force polymer precipitation through a salting-out phenomenon. For example, anionic polymers, such as sodium salts of polyacrylate and carboxymethyl cellulose, become insoluble in an aqueous solution of common salt having a concentration of 4 to 5% or higher; non-ionic polymers such as hydroxyethyl cellulose and polyvinyl alcohol (PVA) are insoluble in an aqueous solution only when the concentration of the salt is increased to about 10% or higher. This salting out of a water soluble polymer describes the change from a homogeneous polymer solution to a polymer precipitate.

While an ion-trigger polymer is certainly salt-sensitive, like the simple water-soluble polymers mentioned above, there are several significant differences in the behavior of an ion-trigger polymer for flushable applications. First, the ion-trigger polymer may be sensitive to changes in ion concentration at low levels, such as 0.5% by weight of a common salt. Second, in the aqueous ionic solutions of typical body fluids, the ion trigger polymer is expected not just to be insoluble, but is required to maintain integrity and strength and act as a barrier coating. Finally, the ion trigger polymer loses enough strength or integrity to disperse in tap water; but note that this dispersion does not necessarily require full dissolution, as would be typical with the simple salt-sensitive water-soluble polymers.

The feature of integrity and strength in use can be achieved by ensuring a proper "hydrophobic/hydrophilic balance" throughout the polymer chain. As used herein, the term "hydrophobic/hydrophilic balance" refers to a balance of hydrophobic and hydrophilic moieties along the polymer chain, which results in the polymer having a desired trigger property. By control of the hydrophobic/hydrophilic balance in the composition of the polymer, ion-sensitive polymers having desired in-use integrity and water dispersibility are produced. In contrast, for simple salt-sensitive, water-soluble homopolymers, like polyvinyl alcohol, the hydrophobic/hydrophilic character is fixed by the structure of the monomer, and cannot be adjusted.

In one formulation of the ion-trigger coating, the ion-trigger character is provided by a sulfonated polyester condensation polymer. The hydrophobic/hydrophilic balance can be controlled by choice of the monomers involved in the condensation reaction. The preparation of such polyesters is generally described, for example, in U.S. Pat. Nos. 4,910,292, 4,973,656 and 4,990,593, and European Patent Application No. EP 0 761 795 A2, all incorporated herein by reference.

In general, the ion-trigger material is a material that acts as a barrier coating thereby inhibiting the transport of fluids through the coating. Preferably, these materials are melt processable since they are easier to apply to a water-soluble substrate. Several different aqueous compounds have ion-triggerability, however, these compounds are not preferred. For example, U.S. Pat. Nos. 5,317,063 and 5,312,883 reveal acrylic acid or methacrylic acid copolymers that are ion-sensitive. Unfortunately, these materials are not melt processable, and so not amenable to melt coating. Coating an aqueous solution of ion-trigger polymers on water-sensitive substrate is difficult as the aqueous nature of these coatings tends to partially dissolve the water-soluble substrate. In addition, the acrylic or methacrylic functionality in the polymer is sensitive to physical crosslinking through divalent ions and therefore would not readily disperse in hard water.

In a desired embodiment of the invention, the ion-trigger polymer coating composition includes at least one water dispersible copolyester, present in an amount from about 25 to 100% by weight. Water dispersible copolyesters are those in which ionic moieties or water sensitive reactants are incorporated into the backbone.

Alternatively, the ionic moieties may be grafted onto the backbone. The structure of such copolyesters are described in Miller, et al., WO 95/18191, incorporated herein by reference. The "Eastman AQ" copolyesters, as taught by Miller, incorporate ionic moieties by copolymerizing 5-sodiosulfoisophthalate units into a polyester backbone. Due to certain deficiencies in the neat polymer, it is often desirable to add a second compatible polymer at concentration up to about 20% by weight to increase the cohesive strength, improve the sprayability, and/or reduce the cold flow tendencies. This second polymer may be any compatible elastomer, such as a thermoplastic block copolymer, an amorphous or crystalline polyolefin such as polypropylene, polybutylene or polyethylene; and ethylenic copolymers such as ethylene-vinyl acetate, ethylene-methyl acetate, and mixtures thereof.

Other useful ion-trigger polymers are described in U.S. Pat. Nos. 5,543,488 and 5,552,495, incorporated herein by reference, which disclose sulfonated copolyesters. Other useful polymer blends are available from National Starch and Chemical Company as NS70-4395 or NS70-4442.

In addition to the sulfonated copolyesters cited above, a variety of other trigger polymers are known in the art. U.S. Pat. No. 5,770,528 reveals methylated hydroxproplyl cellulose as an polymer with trigger controlled by temperature and ion concentration. Hydroxypropyl cellulose itself has some ion-sensitivity, but is more of a temperature trigger material. Indeed, U.S. Pat. No. 5,509,913 lists a variety of polymers, including poly vinyl methyl ether, polyvinyl alcohol and various cellulose polymers with temperature triggers modulated by ion concentration. While these temperature-trigger polymers may have some utility in an ion-trigger coating, these simple polymers themselves do not usually have the proper "hydrophobic/hydrophilic balance" to provide the required integrity and strength in use.

In general, the thickness of the ion-trigger coating layer is dependent upon the product to be made. Preferably, the thickness is between about 0.1 to 3.0 mils. More preferably, the thickness is between about 0.5 to 2.0 mils. Most preferably the thickness is about 0.8 mils.

It may also be desirable to incorporate into the ion-trigger layer up to 20% by weight of certain other hydrophilic non-crystalline polymers such as hydroxyethyl cellulose, hydroxypropyl cellulose, polyvinyl methyl ether, polyvinylpyrrolidone, polyethyloxazoline, starch or cellulose esters, particularly the acetates with a degree of substitution less than 2.5; the latter polymers function to increase the water sensitivity of the ion-trigger coating layer, which may be desired for some applications.

It may also be advantageous to blend the ion-trigger polymer coating composition with a hydrophobic polymer, such as polypropylene, polyethylene, or poly(lactic acid). The hydrophobic polymer can alter both the sensitivity of the ion-trigger composition to the differences between salt solution and pure water, and the time toward barrier failure when the composition is exposed to either salt solution or pure water.

Other hydrophobic compatible polymers include elastomeric polymers such as styrene containing block copolymers, e.g., styrene-isoprene-styrene, epoxidized polyisoprene, styrene-butadiene-styrene, styrene-ethylene butylene-styrene, styrene-ethylene propylene styrene may also be present at levels up to about 30% by weight. Of these polymers, those based on styrene-isoprene-styrene are most preferred. Among the applicable stabilizers or antioxidants which may be included herein are high molecular weight hindered phenols and multifunctional phenols such as sulfur and phosphorous-containing phenols. Representative hindered phenols include:

1,3,5-trimethyl-2,4,6-tris(3,5-di-tert-butyl-4-hydroxyphenyl) propionate; n-octadecyl 3,5-di-tert-butyl-4-hydroxyphenyl) propionate; 4,4'-methylenebis (2,6-di-tert-butylphenol); 4,4'-thiobis (6-tert-butyl-o-cresol); 2,6-di-tert-butylphenol; 6-(4-hydroxyphenoxy)-2,4-bis(n-octylthio)-1,3,5-triazine; di-n-octadecyl-3,5-di-tert-butyl-4-hydroxybenzyl -phosphonate; 2-(n-octylthio)-ethyl 3,5-di-tert-butyl-4-hydroxybenzoate; and sorbitol hexa(3-(3,5-di-tert-butyl-4-hydroxyphenyl)propionate). If used, the stabilizer may be present in levels of 0.1 to 3% by weight.

A plasticizer is broadly defined as a typically organic composition that can be added to thermoplastics, rubbers and other resins to improve extrudability, flexibility, workability, or stretchability. Plasticizers may be used in the ion-trigger layer at concentrations up to about 50% by weight. Preferably, the plasticizing agent is a solid at ambient temperature with a softening point above 60 degrees Celsius, and belongs to the class of plasticizers including cyclohexane dimethanol dibenzoate. Any plasticizer that will recrystallize in the compounded thermoplastic composition is suitable, for example, a 1,4-cyclohexane dimethanol dibenzoate compound commercially available from Velsicol Chemical Corp., Rosemont, Ill., under the tradename BENZOFLEX® 352. Other plasticizers that may be suitable for this purpose are described in EP 0422 108 B1 and EP 0 410 412 B1, both assigned to H. B. Fuller Company, incorporated herein by reference. When combined with the copolyesters, such as the Eastman AQ series, these plasticizers exhibit the unique ability to vastly improve the processability in the molten state, yet not interfere with the dispensability once cooled and solidified.

Other suitable plasticizers include hydrocarbon oils, polybutene, liquid tackifying resins, and liquid elastomers. Such oils are primarily hydrocarbon oils, and are paraffinic or naphthenic in character. The oils are preferably low in volatility, transparent and have as little color and odor as possible. The use of plasticizers in this invention also contemplates the use of olefin oligomers, low molecular weight polymers, vegetable oils and their derivatives and similar plasticizing liquids.

The ion-trigger coating layer may comprise a wax present in amounts up to about 20% by weight, more preferably in amounts ranging from about I to about 10% by weight. The wax is added to modify the viscosity, reduce the tack, and improve the humidity resistance. In one embodiment, the wax is polar in nature such as amide waxes. Other useful waxes include paraffin waxes, microcrystalline waxes, Fischer-Tropsch synthesis products, polyethylene and by-products of polyethylene.

As is known in the art, various other components can be added to modify the tack, color, and odor of a polymer. It is generally preferred that the other components or ingredients should be relatively inert and have negligible effects upon the properties contributed by the copolyester, tackifying agent, and plasticizer. Antioxidants and other stabilizing ingredients can also be added to protect the ion-trigger polymer from various heat and light induced degradation, but are not essential to the compositions of this invention.

Optional additives may be incorporated into the ion trigger polymer coating composition in order to modify certain properties thereof. Among these additives are colorants such as titanium dioxide, and fillers such as talc, clay or other silicates.

For a flushable composition of the present invention, such as a diaper outer cover or a pantiliner baffle, the inner side of the composition—the side closer to the wearer of the article—will typically be exposed to body fluids in use, while both sides will be exposed to toilet water in disposal. The ion-trigger coating on the side adjacent to the wearer of the article inhibits the transport of body fluids through the composition, and provides a barrier between body fluids and the water-dispersible substrate on the outer surface. However, the side of the article further from the wearer of the water-dispersible substrate is designed to quickly weaken in the flow of toilet water, and allows the entire composition to lose enough structural integrity to flush down a conventional toilet. Preferably, the wet substrate has a peak-load strength of less than 20 g/in, which is comparable to wet bathroom tissue.

Suitable polymers for the water-sensitive substrate layer include, but are not limited to, polyalkylene oxides, such as polyethylene oxide (PEO), ethylene oxide-propylene oxide copolymers, polymethacrylic acid, polymethacrylic acid copolymers, polyvinyl alcohol and vinyl alcohol copolymers, polyethyl oxazoline, polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, polyvinyl methyl oxazolidimone, poly(2-isopropyl-2-oxazoline), poly(isopropyl oxazoline), and poly (2,4-dimethyl-6-triazinyl ethylene). The water-sensitive substrate layer of the present invention may be made entirely of water-sensitive polymeric material or may contain water-sensitive as well as water-insoluble materials so long as the film disperses in water, such as in the hydraulic flow of a conventional toilet. Additionally, the water-sensitive substrate may also be made by mixing various different types of water-sensitive film materials. In some embodiments, it may be desirable to employ one or more additives into the water-sensitive substrate layer material including, but not limited to, compatibilizers, processing aids, plasticizers, tackifiers, detackifiers, slip agents, and anti-microbial agents, as fabricating agents or as modifiers depending on the specific properties desired in the water-sensitive substrate and the final product.

Desirably, the water-sensitive substrate of the present invention comprises a polyalkylene oxide film or a polyvinyl alcohol film. More desirably, the water-sensitive substrate of the present invention comprises a polyethylene oxide film, an ethylene oxide-propylene oxide copolymer film, a polyvinyl alcohol film or a film derived from a polyvinyl alcohol copolymer. Most desirably, the water-sensitive substrate of the present invention comprises a polyethylene oxide film or a polyvinyl alcohol film. The thickness of the water-sensitive substrate may vary greatly depending upon the end use of the film-containing product. The thickness of the water-sensitive substrate should be minimized when possible to reduce product cost and to reduce the time necessary for the substrate to disperse, especially in the case of flushable products. Desirably, the water-sensitive substrate thickness will be as thin as possible, depending upon the product to be made. Preferably, the thickness will be from about 0.1 to 3.0 mil.

In the uncoated form, when the water-sensitive substrate contacts water on either surface, it disperses. In the ion-trigger coated form, when only the outer side of the water-sensitive substrate contacts water, the composite two-layer structure will not immediately disperse, due to the transient structural integrity of the ion-trigger coating. However, the composite two-layer composition is dispersible when both the ion-trigger coating and the water-sensitive substrate have been exposed to water for some time.

The coating of ion-trigger polymer provides the required barrier to ion containing body fluids, yet weakens and disperses in relatively low-ion containing toilet water. In the presence of an aqueous salt solution, such as urine, the ion-trigger polymer is relatively inert. Water from the salt solution can reach the substrate only by a slow process of diffusion through the coating. However, the ion-trigger polymer rapidly weakens in tap water. The process of water penetration in the coating will differ with the ion content of the aqueous solution.

The ion-trigger layer may be joined to the water-dispersible substrate by standard methods known to those of ordinary skill in the art. As mentioned, the ion-trigger layer itself can provide enough tack to join the water-sensitive substrate layer thereto. Other suitable methods of joining the layers include, but are not limited to, solvent-based coating and holt-melt coating. Suitable solvent-based coating techniques include, but are not limited to, spray coating and ink jet printing. Suitable hot-melt coating techniques include, but are not limited to, slot coating, screen coating, spray coating, swirl coating and gravure coating. Another suitable method includes a transfer coating procedure.

The preferred coating process is a hot-melt slot die process. Molten ion-trigger polymer is delivered from a melting tank through a heated hose to a slot die. The temperature of the melting tank, hose and slot die may vary depending upon the melt rheology of the ion-trigger in the coating process. The molten polymer is uniformly applied directly onto the water-sensitive film, or alternatively, onto a carrier substrate and subsequently transferred onto the water-sensitive film (transfer coating process). Line speeds may vary depending upon the "open time" of the ion-trigger. As used herein, the "open time" of a polymer refers to the amount of time required for the polymer to lose its tackiness.

The polyethylene oxide film is the most desirable film for a transfer coating procedure, while the polyvinyl alcohol film is the most desirable film for a direct coating procedure.

In a transfer coating process, the coated carrier substrate moves further through the process and comes into contact with the water-sensitive film, which is properly aligned with the coated carrier substrate. The coating is transferred from the carrier substrate to the water-sensitive film under pressure as the film and carrier substrate pass through a nip roll. In practice, optimum coating thickness is achieved by adjusting processing factors which include, but are not limited to, the coating temperature, the resin flow rate, line speed, and the pressure applied at the nip roll.

In the transfer coating process or in a direct contact coating process, such as screen printing, the adhesion of the ion-trigger coating to the water-sensitive film should be greater than the adhesion of the ion-trigger coating to the screen (direct coating) or the carrier substrate (transfer coating). The choice of ion-trigger should take into consideration the desired characteristics and properties of the ion-trigger. The ion-trigger should have good adhesion to the water-sensitive substrate.

Those skilled in the art will readily understand that the ion-trigger coated water-dispersible films of the present invention may be advantageously employed in the preparation of a wide variety of products designed to be contacted with aqueous fluids. Although the coated water-dispersible film of the present invention is particularly suited for personal care products, the coated water-dispersible film of the present invention may be advantageously employed in the preparation of a wide variety of consumer products other than personal care products.

EXAMPLES

Example 1

A two layer composite structure was produced by coating an ion-trigger blend from National Starch and Chemical Company (Bridgewater, N.J.), resin coded NS70-4395, onto a polyethylene oxide film made from resin. compounded and pelletized by Planet Polymer Technologies Inc. (San Diego, Calif.). The blend was characterized in terms of its melt viscosity, as measured on a capillary rheometer (Göttfert Rheograph 2003, Göttfert Werkstoff-Prüfmaschinen GmbH, Buchen, Germany). Viscosity data is reported in Table 1. As appropriate for a coating application, this material was classified as a moderate or low viscosity fluid at the application temperature of about 150° C. The coating was applied with an Acumeter Laboratories Inc. precision slot die coater to AKROSIL® release paper (Akrosil, Menasha, Wis.) and then transferred to the polyethylene oxide substrate. Coated films were prepared with ion-trigger coating thicknesses of 0.5, 1.0, 1.5 and 2.0 mil.

The barrier properties of these films were then tested in the lab with a modified Cobb's test. In the standard Cobb's test for water uptake in a film (American Society for Testing and Materials [Philadelphia, Pa.] D3285, Technical Association of the Pulp and Paper Industry T441) a fixed surface area of film, clamped under a steel ring, is held under a pool of water, standing at 1 centimeter depth, for a fixed time; the weight gain in the film due to water absorption, from the initial dry state to the final, blotted-dry state, is measured. In these experiments, the test was modified from a weight-gain method to a visual-indicator test by introducing a layer of pH paper (Hydrion paper for range 3.5 to 5.5 pH, Hydrion Papers Inc. [Brooklyn, N.Y. 11210]) under the film. The pH paper turns from orange to green-green/blue when exposed to water and saline solution; the pH paper changes color in the same manner when exposed to a wetted polyethylene oxide film laying on top of it. The color change gave a visual indication of the time at which water permeated through the barrier coating and then wetted the polyethylene oxide substrate.

The time for water to permeate through the coated film was monitored as a function of film thickness and fluid type. Two fluids were used: distilled water, as a mimic of toilet water, and two percent sodium sulfate solution, as a mimic of urine. In distilled water, all the coatings failed in under one minute, as indicated by a change in color of pH paper from orange to blue-green. In salt solution, the time for water permeation depended on the film thickness. The 2.0 mil ion-trigger coating provided protection for over 30 minutes on average, as the color of pH paper did not change. The thinnest coating protected against water leakage only for less than 1 minute. The experiments indicate that, even in salt solution, the trigger coating is hydrated by water. In salt solution, the hydration is a slow process, and appears to be diffusion controlled. The level of barrier protection against salt solution can be controlled (up to a time of 30 minutes) by the thickness of the film.

As a measure of dispersability of the coated films, their wet strength was also tested. A one-inch by four-inch sample of film was clamped by the short sides in a Vitrodyne V-1000 mini tensile tester from Chattilon (Greensboro, N.C.), and then submerged, clamps and all, in a beaker of fluid. The fluid comprised either distilled water or a salt solution After 30 seconds, the sample was pulled apart and the peak load measured. The peak load in distilled water was substantially less than the strength in salt solution. In distilled water, the strength of a 2.0 mil coating was slightly higher than that of wet toilet tissue, while the strength of a 1.0 mil coating was less than toilet tissue. This data indicates that when wetted in toilet water, the coated film should be weak enough to disperse.

Example 2

A higher melt viscosity version of a trigger blend was obtained from National Starch, coded NS70-4442, and was coextruded with poly(ethylene oxide). The viscosity characteristics of this resin, which again were measured on a capillary rheometer (Göttfert Rheograph 2003, Göttfert WerkstoffPrüfmaschinen GmbH, Buchen, Germany) are reported in Table 1. As appropriate for a coextruded application, the viscosity of the NS770-4442 was appreciably higher than for the NS70-4395 of Example 1. The film contained poly(ethylene oxide) made from resin compounded and pelletized by Planet Polymer Technologies, Inc. (San Diego, Calif. 92131). In the two layer structure, the trigger resin formed a thin coating, with nominal thickness 0.4 mil. The barrier performance of this coextruded coating was consistent with the coatings from a slot die. While water penetration was essentially instantaneous, salt solution was held away from the polyethylene oxide substrate for about one minute. At the same time the wet strength in both water and salt solution was higher than found in the 1.0 mil slot coating (and higher than toilet tissue). These results were obtained by using a one-inch by four-inch sample of film that was clamped by the short sides in a Vitrodyne V-1000 mini tensile tester, and then submerged, clamps and all, in a beaker of fluid. The fluid comprised either distilled water or a salt solution After 30 seconds, the sample was pulled apart and the peak load measured.

TABLE 1

| Material | Temperature (° C.) | Shear Rate (l/second) | Shear Stress (Pa) | Viscosity (Pa · S) |
|---|---|---|---|---|
| 70-4395 | 180 | 1000 | 24,630 | 24.6 |
| 70-4442 | 160 | 1000 | 88,544 | 88.5 |
| 70-4442 | 170 | 1000 | 64,118 | 64.1 |
| 70-4442 | 180 | 1000 | 46,613 | 46.6 |
| 70-4442 | 190 | 1000 | 33,382 | 33.4 |

It is to be understood that the above-disclosed embodiments are merely illustrative and are not intended to limit the scope of the invention. On the contrary, other embodiments will become obvious to one skilled in the art in light of the disclosure of the present invention and all such obvious variations are contemplated within the scope of the appended claims.

We claim:

1. A flushable film comprising a melt-processable ion-trigger polymer coating on a water-sensitive substrate layer;

wherein the ion-trigger polymer coating further comprises a hydrophilic non-crystalline polymer selected from hydroxyethyl cellulose, hydroxypropyl cellulose, polyvinyl methyl ether, polyvinylpyrrolidone, polyethyloxazoline, starch, a cellulose ester, or a mixture thereof.

2. The flushable film of claim 1, wherein the water-sensitive substrate layer is comprised of a polymer selected from polyalkylene oxides, polyethylene oxide or ethylene oxide-propylene oxide copolymers, polymethacrylic acid, polymethacrylic acid copolymers, polyvinyl alcohol, polyvinyl alcohol copolymers, polyethyl oxazoline, polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, polyvinyl methyl oxazolidimone, poly(2-isopropyl-2-oxazoline), or poly (2,4-dimethyl-6-triazinyl ethylene).

3. The flushable film of claim 2, wherein the water-sensitive substrate layer comprises polyethylene oxide.

4. The flushable film of claim 1, wherein the ion-trigger polymer coating is between 0.1 and 3.0 mil in thickness.

5. The flushable film of claim 1, wherein the water-sensitive substrate layer is between 0.1 and 3.0 mil in thickness.

6. The flushable film of claim 1, wherein the melt-processable ion-trigger polymer is selected from copolyesters, copolyesters having an ionic moiety grafted thereto, sulfonated copolyesters, or methylated hydroxproplyl cellulose.

7. The flushable film of claim 1, wherein the hydrophilic non-crystalline polymer is added in an amount greater than 0 to about 20% by weight of the ion-trigger polymer.

8. The flushable film of claim 1, wherein the ion-trigger polymer coating further comprises a hydrophobic polymer selected from polypropylene, polyethylene, poly(lactic acid) or a styrene-containing block copolymer.

9. The flushable film of claim 1, wherein the ion-trigger polymer coating further comprises a hydrophobic polymer selected from polypropylene, polyethylene, poly(lactic acid) or a styrene-containing block copolymer.

10. The flushable film of claim 9, wherein the hydrophobic polymer is added in an amount greater than 0 to about 30% by weight of the ion-trigger polymer.

11. The flushable film of claim 1, wherein the ion-trigger polymer coating further comprises a stabilizer and/or antioxidant selected from high molecular weight hindered phenols, sulfur-containing phenols or phosphorous-containing phenols.

12. The flushable film of claim 1, wherein the ion-trigger polymer coating further comprises a plasticizer.

13. The flushable film of claim 12, wherein the plasticizer is added in an amount greater than 0 to about 50% by weight of the ion-trigger polymer.

14. A flushable product comprising:

the flushable film of claim 1; and at least one additional layer adhered to the flushable film.

15. The flushable product of claim 14, wherein the flushable product is selected from a personal care article, a medical care article, a packaging material, or a release film.

16. A method of making a flushable film comprising:

forming a layer of a melt-processable ion-trigger polymer on a water-sensitive substrate layer; wherein the ion-trigger polymer coating further comprises a hydrophilic non-crystalline polymer selected from hydroxyethyl cellulose, hydroxypropyl cellulose, polyvinyl methyl ether, polyvinylpyrrolidone, polyethyloxazoline, starch, a cellulose ester, or a mixture thereof.

17. The method of claim 16, wherein the melt-processable ion-trigger polymer is formed on the water-sensitive substrate layer by simultaneously generating the two layers in a coextrusion process.

18. The method of claim 16, wherein the melt-processable ion-trigger polymer is formed on the water-sensitive substrate layer by coating the melt-processable ion-trigger polymer onto the water-sensitive substrate.

19. The method of claim 18, wherein the melt-processable ion-trigger polymer is coated using a coating process selected from a direct coating process or a transfer coating process.

20. The method of claim 7, wherein the water-sensitive substrate layer is comprised of a polymer selected from polyalkylene oxides, polyethylene oxide or ethylene oxide-propylene oxide copolymers, polymethacrylic acid, polymethacrylic acid copolymers, polyvinyl alcohol, polyvinyl alcohol copolymers, polyethyl oxazoline, polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, polyvinyl methyl oxazolidimone, poly(2-isopropyl-2-oxazoline), or poly (2,4-dimethyl-6-triazinyl ethylene).

21. The method of claim 20, wherein the water-sensitive substrate layer comprises polyethylene oxide.

22. The method of claim 16, wherein the ion-trigger polymer coating is between 0.1 and 3.0 mil in thickness.

23. The method of claim 16, wherein the water-sensitive substrate layer is between 0.1 and 3.0 mil in thickness.

24. The method of claim 16, wherein the melt-processable ion-trigger polymer is selected from copolyesters, copolyesters having an ionic moiety grafted thereto, sulfonated copolyesters, or methylated hydroxproplyl cellulose.

* * * * *